United States Patent [19]

Katamine et al.

[11] Patent Number: 5,219,762
[45] Date of Patent: Jun. 15, 1993

[54] METHOD AND DEVICE FOR MEASURING A TARGET SUBSTANCE IN A LIQUID SAMPLE

[75] Inventors: Tomoaki Katamine, Urawa; Hiroshi Sato, Kitakatsushika; Ei Mochida, Tokyo, all of Japan

[73] Assignee: Mochida Pharmaceutical Co., Ltd., Tokyo, Japan

[21] Appl. No.: 454,018

[22] Filed: Dec. 20, 1989

[30] Foreign Application Priority Data

Dec. 27, 1988 [JP] Japan .................. 63-330300

[51] Int. Cl.⁵ .............................................. G01N 15/00
[52] U.S. Cl. ................................ 436/518; 436/512; 436/514; 436/531; 436/807; 436/177; 436/180; 436/46; 435/4; 435/6; 435/288; 435/805; 422/57; 422/58; 422/60; 422/61; 422/68.1
[58] Field of Search ................ 422/58, 60, 61, 68.1, 422/57; 435/6, 288, 4, 805, 920; 436/46, 177, 180, 512, 514, 518, 531, 807

[56] References Cited

U.S. PATENT DOCUMENTS

| | | | |
|---|---|---|---|
| 3,791,933 | 2/1974 | Moyer et al. | 422/56 |
| 4,578,349 | 3/1986 | Schaffel | 436/177 |
| 4,631,254 | 1/1986 | Giorgio et al. | 436/177 |
| 4,647,430 | 3/1987 | Zweig | 422/56 |
| 4,780,282 | 10/1988 | Holtzclaw et al. | 422/56 |
| 4,916,056 | 4/1990 | Brown, III et al. | 422/56 |
| 4,994,238 | 2/1991 | Daffern et al. | 422/57 |

FOREIGN PATENT DOCUMENTS 0212634 4/1987 European Pat. Off. .
WO88/07679 10/1988 PCT Int'l Appl. .

*Primary Examiner*—James C. Housel
*Assistant Examiner*—Harold Y. Pyon
*Attorney, Agent, or Firm*—Burns, Doane, Swecker & Mathis

[57] ABSTRACT

A method for measuring target substance contained in a liquid sample is disclosed. The measurement is carried out by using a device having at least one reaction area comprising a solid phase, and the liquid sample is applied onto the reaction area through a porous member to allow for a reaction of predetermined volume of the liquid sample on the reaction area. A device used for such measurement is also disclosed. A device comprises a body having at least one reaction area comprising a solid phase, and a porous member disposed on or above the reaction area. The porous member allows for the liquid sample to be permeated therethrough.

23 Claims, 8 Drawing Sheets

F I G. 5
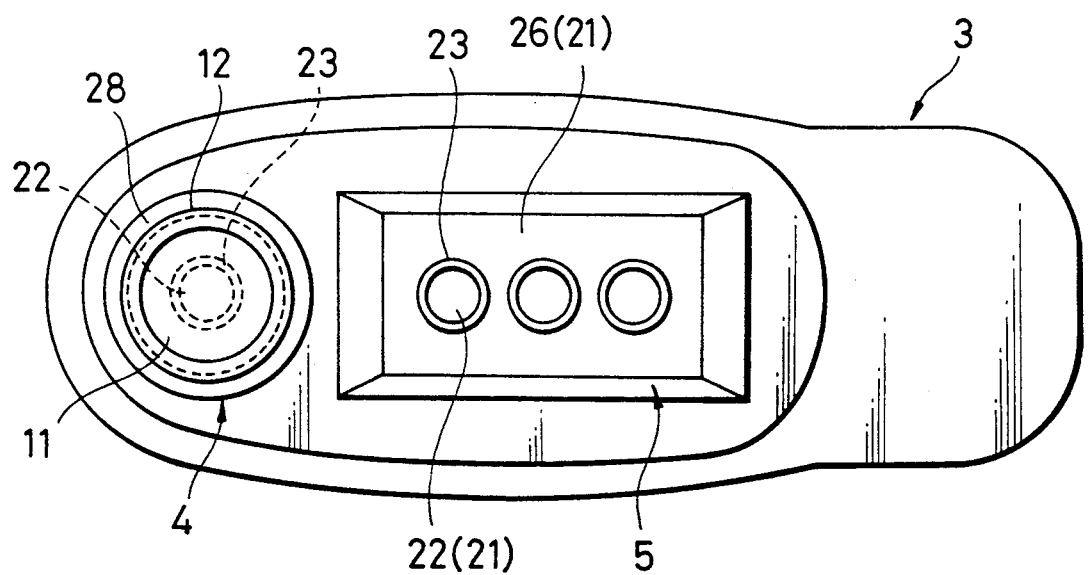

METHOD AND DEVICE FOR MEASURING A TARGET SUBSTANCE IN A LIQUID SAMPLE

BACKGROUND OF THE INVENTION

This invention relates to a method for quantitatively, semi-quantitatively, or qualitatively detecting a target substance in a predetermined volume of a liquid sample. This invention also relates to a device for measuring the target substance in the liquid sample used for carrying out said method, which has a structure capable of collecting a predetermined volume of the liquid sample.

Various methods for measuring a target substance in a liquid sample by allowing a reaction of said target substance on a solid phase are currently available.

Typical examples of such methods include methods wherein a target substance in a liquid sample is physically adsorbed on a solid phase, a binding substance which specifically binds to the target substance to be measured is bound to the target substance adsorbed on the solid phase, and amount of the binding substance bound to the target substance to be measured is determined by means of radioactivity, color development, fluorescence, luminescence, and the like.

In other typical methods, a reactive substance which specifically reacts with the target substance in the liquid sample or the binding substance is immobilized on a solid phase, the liquid sample is applied onto the solid phase on which the reactive substance or the binding substance has been immobilized, and the amount of the target substance in the liquid sample is determined by means of the reaction between the target substance and the reactive substance or the binding substance.

In the methods utilizing the binding substance, binding reactions such as antigen-antibody reaction, nucleic acid hybridization reaction, and receptor-ligand reaction are carried out on the solid phase by using binding substances such as antigen, antibody, antibody fragment, nucleic acid, lectin, receptor, and ligand.

The methods utilizing the reactive substance include enzymatic methods wherein an enzyme whose substrate is the target substance in the liquid sample is immobilized on the solid phase, the liquid sample is applied to the solid phase on which the enzyme has been immobilized, and concentration of the target substance in the liquid sample is measured by detecting the enzymatic reaction on the solid phase between the enzyme and the substrate which is the target substance. Typical enzymatic measurements include measurements of glucose by using glucose oxidase and peroxidase, urea nitrogen by using urease and indophenol, cholesterol by using cholesterol oxidase and cholesterol esterase, GOT by using malate dehydrogenase and NADH, and GPT by using lactate dehydrogenase and NADH, which are mainly utilized in urinalysis and hemanalysis.

The methods for measuring the target substance in the liquid samples using the above-mentioned reactions on the solid phase are widely employed in such applications as clinical examinations because of their simple measuring procedure as well as high accuracy, specificity and sensitivity. Among such methods, those utilizing sheet-like solid phase are particularly useful since they are capable of measuring the target substance in a minute amount of liquid sample as well as accurately measuring liquid samples such as nipple discharge whose properties including viscosity and protein concentration are, unlike urine or serum, significantly different from sample to sample.

A typical method for measuring the concentration of a target substance in a liquid sample by utilizing the reaction on a sheet-like solid phase is disclosed in Japanese Patent Application No. 63-252357 filed by the inventors of the present invention. This method relates to a method for detecting a target substance such as tumor-associated antigen, particularly CEA (carcinoembryonic antigen), in a minute amount of nipple discharge. This method has enabled a detection at an early stage of mammary cancer in patients exhibiting abnormal secretion of nipple discharge. In particular, this method has enabled a detection at a quite high sensitivity of mammary cancer with no tumor, which is likely to be missed by palpation or visual examination in cancer screenings. This method has also enabled a simple and accurate measurement.

The method disclosed in Japanese Patent Application No. 63-252357, supra has also enabled to measure concentration of the target substance in such sample as nipple discharge, whose viscosity varies from sample to sample and which is collected not more than about 10 $\mu$L at a time. In this method, the liquid sample is applied to a relatively large area on the sheet-like solid phase, and therefore, the sample contacts with a larger amount of the substance such as antibody which specifically binds to the target substance to be measured. Thickness of the thus applied sample liquid phase to be measured may also be decreased to increase the reactivity and minimize effects on the measurements of the properties of the sample such as viscosity. Accordingly, this method may be utilized in such cases wherein sample collection using conventional collecting devices including pipette and capillary is difficult to carry out and wherein the sample volume is to small to measure. Nonspecific adsorption of the non-specific constituents in the sample onto the solid phase is also suppressed by selecting an appropriate material for the sheet-like solid phase.

Since the non-specific constituents included in the sample may be easily removed by washing the solid phase either before or after the drying of the liquid sample on the solid phase irrespective of the viscosity of the sample, properties of the sample as well as the drying of the sample least affected the results obtained by this method. This is a marked advantage for such scene as mass screening wherein a large number of samples are occasionally collected, since once collected and dried samples may be left as they are until a sufficient number of samples are collected to resume subsequent procedure.

In most of the prior art methods for measuring the concentration of the target substance in a liquid sample, a sufficient volume of the liquid sample is collected to either immerse the reaction area of the solid phase therein or apply the sample on the reaction area although the volume of the liquid sample required may differ from method to method, and the reaction is then promoted either on the solid phase immersed in the liquid sample or on the solid phase onto which the liquid sample has been applied to determine the concentration of the target substance by means of the thus promoted reaction.

When the reaction on the solid phase depends on the concentration of the target substance in the liquid sample and not on the volume of the liquid sample, namely, the absolute quantity of the target substance in the sample, any desired volume of the liquid sample may be brought into contact with the liquid phase so long as the volume of the liquid sample is sufficient for immersing the reaction area of the solid phase in the sample or applying the sample onto the reaction area.

This is the case for some of the reagents utilizing an enzymatic reaction on the solid phase for their measurements, for example, urinalysis reagents wherein the solid phase is immersed in any desired volume of urine collected in a cup so that the enzymatic reaction may take place on the solid phase.

On the other hand, when the reaction on the solid phase depends not only on the concentration of the target substance in the liquid sample but also on the amount of the liquid sample, namely, the absolute quantity of the target substance in the sample, a predetermined volume of the sample should be brought into contact with the solid phase. This is the case for some of the reagents utilizing an enzymatic reaction on the solid phase and most of the reagents utilizing a binding reaction on the solid phase for their measurements.

As set forth above, simple, convenient methods are known for measuring a target substance in a liquid sample.

These prior art convenient measurements may be employed for the cases wherein the reaction on the solid phase depends solely on the concentration of the target substance in the liquid sample and not on the amount of the liquid sample, namely, the absolute quantity of the target substance in the sample. Even when the reaction depends on the amount of the liquid sample, such prior art measurements are sufficient for limited applications wherein either qualitative results in the form of positive/negative determination or semi-quantitative results are the only results pursued since the amount of the liquid sample collected is not so critical in such measurements.

When a predetermined volume of the liquid sample must be collected for quantitative measurements of the target substance, an additional step of measuring a predetermined volume of the liquid sample would be necessary for each of the sample collected, requiring devices such as pipette and measuring cup for dispensing the sample. When a large number of the liquid sample are to be measured, the time consumed for such a troublesome step becomes non-negligible to result in a decreased efficiency of the measurements. When the volume of the sample collected is minute, in particular, such an additional step should be carried out accurately with great care. Moreover, when properties of the sample such as viscosity are inconsistent, or when a precise collection of the sample by pipette or capillary is difficult due to high viscosity, the step of collecting a predetermined volume of the liquid sample may become a serious obstacle for the measurement.

As set forth above, there is a strong demand for the development of a measurement allowing for a substantially constant volume of the liquid sample to be conveniently collected onto the solid phase and allowing for the target substance to be determined at any desired time either before or after the drying or solidification of the collected liquid sample on the solid phase, especially in such a scene as mass screening wherein a large number of the liquid samples are to be collected, and particularly for the collection of such a sample as nipple discharge wherein a minute volume of the sample having inconsistent properties is to be collected.

To fulfill the above-described social requirements, the inventors of the present invention have carried out an investigation to develop a method and a device capable of collecting a predetermined volume of the liquid sample even when the volume of the liquid sample is minute as well as capable of measuring the volume of the target substance in the liquid sample by a simple operation, and found a structure capable of retaining a substantially constant volume of the collected liquid sample within the reaction area in course of measuring the target substance in the liquid sample by means of a reaction on the solid phase. The present invention was completed on the basis of such a finding.

It is accordingly an object of the present invention to provide a method for collecting a predetermined volume of a liquid sample to quantitatively, semi-quantitatively, or qualitatively detect a target substance contained in the liquid sample.

Another object of the present invention is to provide a device for measuring the target substance in the liquid sample for carrying out said method, comprising a structure capable of collecting a predetermined volume of the liquid sample.

SUMMARY OF THE INVENTION

A first aspect of the present invention is to provide a method for measuring a target substance contained in a liquid sample by using a device having at least one reaction area comprising a solid phase wherein said liquid sample is applied onto said reaction area comprising said solid phase through a porous member to allow for a reaction of predetermined volume of said liquid sample on said reaction area.

A second aspect of the present invention is to provide a device for measuring a target substance in a liquid sample comprising a body having at least one reaction area comprising a solid phase, and a porous member disposed on or above said reaction area, said porous member allowing permeation of said liquid sample therethrough.

According to the present invention, a constant volume of liquid sample may be collected by a simple operation, and a target substance contained in the liquid sample may be measured by means of a reaction on a reaction area comprising a solid phase. The reaction of a constant volume of the liquid sample on the reaction area is realized by applying the liquid sample through a porous portion of a porous member to the reaction area.

These and other objects, aspects, and advantages of this invention will become apparent from the following detailed description taken in connection with the accompanying drawings.

BRIEF DESCRIPTION OF THE DRAWINGS

The invention will now be described with reference to the accompanying drawings wherein.

FIG. 5 is a plan view of further preferred embodiment of the device having a standard-measuring portion in accordance with the present invention;

DETAILED DESCRIPTION OF THE INVENTION

A method for measuring a target substance in a liquid sample, which is the first aspect of the present invention, in hereinafter described in detail with reference to the drawings.

FIGS. 1a, 1b, 1c, 1d, and 1e are schematic drawings illustrating the steps of collecting the liquid sample according to a preferred embodiment of the present invention.

Figure 1A:
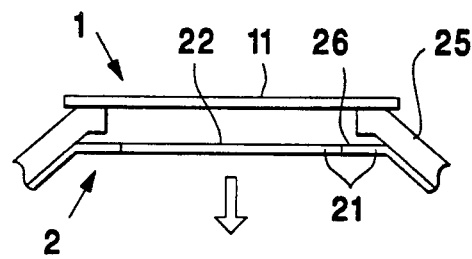
FIGS. 1a, 1b, 1c, 1d, and 1e are schematic drawings sequentially illustrating the method for measuring a target substance in accordance with the present invention.

FIG. 1a shows the device of the present invention before application of the liquid sample. In this embodiment, the device comprises a body 2 and a porous member 1. The body 2 of the device supports a solid phase 21 comprising a reaction area 22 and a non-reaction area 26. Above the solid phase 21, there is removably mounted a porous (net) portion 11 of the porous member 1. The distance between the net portion 11 and the reaction area 22 is kept constant by a frame member 25 which is mounted between the solid phase 21 and the net portion 11. The net portion is stretched by the frame member 25.

The structures of the body 2 and the porous member 1 of the device are not limited to the above-described embodiment. The structures shown in FIGS. 2a and 2b, which will be described later in detail, are also preferred. In the embodiment shown in FIG. 2a, the porous portion 11 of the porous member 1 is in contact with the reaction area 22, while the porous portion 11 and the reaction area 22 are intervened by a supporting member 12 of the porous member 1 in the embodiment shown in FIG. 2b.

Figure 1B:
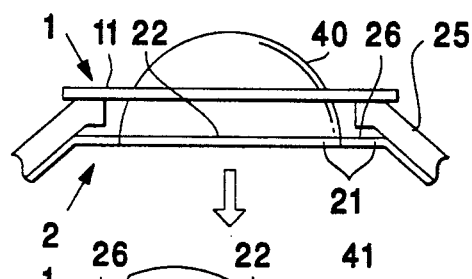
Figure 1C:
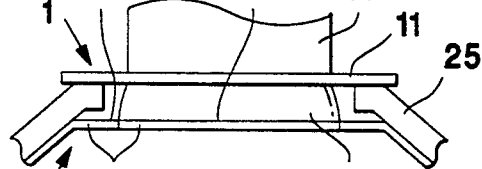

A liquid sample 40 is applied onto the net portion 11 as shown in FIG. 1b, and an excess volume of the liquid sample 40 on the net portion 11 is removed by a remover 41 as shown in FIG. 1c. The step of removing an excess volume of the liquid by the remover 41 as carried out in the present embodiment, however, is not critical in the present invention.

Figures 1, 1D:
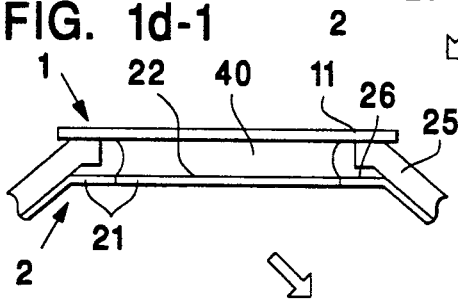
Figures 1, 1D, 2:
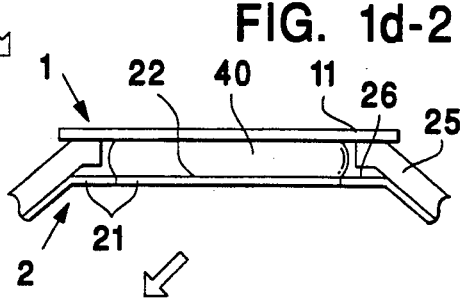
Figure 1E:
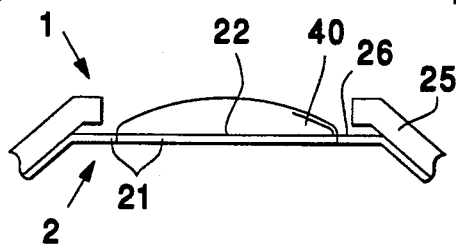

The remover 41 and the porous member 1 are subsequently removed from the device as shown in FIGS. 1d and 1e, and a predetermined volume of the liquid sample 40 is left on the reaction area 22 of the solid phase 21 so that the target substance in the liquid sample 40 would be bound or adsorbed on the reaction area 22 allowing for a reaction to occur thereon to permit for the quantity of the target substance to be measured. It is to be noted that the porous member 1 may not be removed from the device.

Typical of the target substances to be determined by the process of the present invention are substrates for enzymes including $\beta$-D-glucose which is the substrate for glucose oxidase, hydrogen peroxide which is the substrate for peroxidase, urea which is the substrate for urease, cholesterol which is the substrate for cholesterol oxidase, cholesterol ester which is the substrate for cholesterol esterase, oxaloacetic acid which is the substrate for malate dehydrogenase, and lactic acid which is the substrate for lactate dehydrogenase.

Also included in the target substance to be determined by the present process are antigens, haptens, antibodies and their fragments, nucleic acids, lectins, receptors, and ligands.

Typical antigens and haptens include tumor-associated antigens whose concentration in blood has been measured by various method, such as CEA (carcinoembryonic antigen), AFP (alpha-fetoprotein), TPA (tissue polypeptide antigen), and various cancer-associated antigens recognized by monoclonal antibodies, such as CA19-9, CA125, TAG72, CA15-3. The antibodies may be either polyclonal or monoclonal, and include not only purified antibodies but also crude antibodies such as antisera and salted-out antibodies which contain antibodies having binding activity to particular substances. The antibody fragment is a part of an antibody molecule which has the binding activity to antigen, and typical fragments are Fab and F(ab)$_2$. Typical nucleic acids are pathogen genomes such as virus genomes, and typical receptors are hormone receptors such as estrogen receptor and progesterone receptor. Antigens of pathogenic microorganisms and antibodies against pathogenic microorganisms may also be utilized.

Typical of the liquid samples which may be determined by the process of the present invention are blood, serum, plasma, urine, perspiration, tear, saliva, sputum, nipple discharge, cell culture, tissue extract, tissue washing, and other liquids which are expected to contain a target substance to be determined. The liquid sample may either be diluted or non-diluted.

In the process of the present invention, the liquid sample may be collected by means of collecting devices such as pipette and capillary. The samples, however, may also be collected by bringing the device of the present invention in contact with the liquid sample so that the sample is directly collected through the porous portion of the porous member, particularly when a minute volume of a viscous sample is to be collected as in the case of collecting nipple discharge.

The excess portion of the liquid sample is removed in the course of removing the porous member, particularly when the liquid sample is viscous. The excess portion of the liquid sample on the porous portion of the porous member, however, may preferably be removed by employing a remover. In the present invention, a spatula and liquid absorbable materials (such as porous polyethylene or polyurethane, filters or cloths) are used as a remover. When a spatula is used as a remover, the excess portion of the liquid sample on the porous portion of the porous member is scraped from the porous portion with the spatula. When a liquid absorbable material is used as a remover, the remover is brought into contact with the upper surface of the porous portion of the porous member or with the liquid sample remaining on the porous portion of the porous member, and the excess portion of the liquid sample is absorbed by the liquid absorbable material and removed. Accuracy of the volume of the liquid sample involved in the reaction would be improved by including the step of removing the excess liquid sample by the remover.

Typical processes for determining the amount of the target substance to be measured include the following methods.

First method comprises the steps of physically adsorbing the target substance contained in the liquid sample to be measured onto the reaction area comprising the solid phase, and applying thereto a substance which specifically binds or reacts with the target substance to determine the quantity of the target substance on the basis of an indication exhibited by the substance which has specifically bound or reacted with the target substance.

In this method, various substances other than the target substance which are contained in the liquid sample may also be physically adsorbed on the reaction area. Such binding of the substances other than the target substance may be minimized by selecting an appropriate material for the solid phase.

Even when the substances other than the target substance are adsorbed on the reaction area, the quantity of the target substance can still be measured despite the precision of the measurement may become somewhat degraded, since the measurement of the target substance in this method is based on the indication exhibited by the substance which specifically binds or reacts with the target substance to be measured.

The second method, which is more preferable than the first method, comprises the steps of insolubilizing a substance which specifically binds to or reacts with the target substance to be measured in the liquid sample onto the reaction area comprising the solid phase, and applying thereto a substantially predetermined volume of the liquid sample in the above-described manner.

The second method is hereinafter described for a case wherein the target substance to be measured in the liquid sample is an antigen.

In this case, an antibody or a fragment thereof (hereinafter referred to as an antibody) against the antigen is preliminarily immobilized on the reaction area comprising a solid phase, and a substantially predetermined volume of the liquid sample is applied to allow for the antigen to be determined in the liquid sample to bind to the immobilized antibody. Thereafter, a labelled antibody, which is an antibody capable of specifically binding to the antigen and having bound thereto a labelling agent for indicating the volume of the antigen, is reacted with the antigen to measure the quantity of the antigen in the liquid sample on the basis of an indication exhibited by the labelled antibody. This method is called a sandwich method.

The quantity of the antigen may also be determined by a competitive method. In the competitive method, a predetermined amount of an antibody against the antigen to be measured is preliminarily immobilized on the reaction area comprising a solid phase, and a substantially predetermined volume of the liquid sample and a known amount of labelled antigen are applied thereto to determine the quantity of the antigen in the liquid sample on the basis of an indication exhibited by the labelled antigen.

The second method is further described with regard to a case wherein the target substance to be measured in the liquid sample is a substrate for an enzyme. In this case, an enzyme is preliminarily immobilized on the reaction area comprising a solid phase by a site other than the active center of the enzyme, and a substantially predetermined volume of the liquid sample is applied thereto to determine the quantity of the target substrate in the liquid sample on the basis of an indication generated by the reaction between the enzyme and the substrate, which is the target substance to be measured in the liquid sample.

Among the methods described above, the second group of methods are more sensitive than the first method. Of the second group, the sandwich method is less likely to be affected by the components in the liquid sample other than the target substance to be determined, and capable of readily controlling measuring sensitivity and measurable concentration range. Therefore, the sandwich method is most preferable.

The sandwich method may be carried out in the three manners as described below, which differs from one another in the order of reaction of the three components involved in the measurements, which are the substance which specifically binds to the target substance to be measured being insolubilized onto the reaction area comprising a solid phase, the target substance to be measured, and the labelled substance which specifically binds to the target substance to be measured.

The three manners of sandwich method are hereinafter described for the case wherein the target substance to be measured is an antigen.

(1) To the reaction area onto which the antibody has been immobilized, a liquid sample which is expected to contain the antigen is applied to allow for a reaction to occur, and the labelled antigen is applied thereto to allow for another reaction to occur. Thereafter, the components of the liquid sample and the labelled antibody which failed to bind the antibody insolubilized onto the reaction area are removed by rinsing, and the quantity of the antigen in the liquid sample is measured by means of the quantity of the labelled antibody which were bound to the reaction area.

(2) To the reaction area onto which the antibody has been immobilized, the labelled antibody is also preliminarily applied. And the liquid sample which is expected to contain the antigen is applied thereto to allow for a simultaneous reaction among the three components.

(3) To the reaction area onto which the antibody has been immobilized, a mixture of the liquid sample collected and the labelled antibody is applied to allow for a reaction to occur.

In method (2), an optional lyophilization may be carried out after applying the labelled antibody onto the reaction area to which the antibody has been preliminarily immobilized in order to improve the stability of the reagents including the labelled antibody.

Of the three manners of the sandwich method, the manners (1) and (2) are preferable for such case as nipple discharge wherein the sample volume is minute or the sample is viscous since the process in accordance with the present invention is capable of directly collecting a substantially predetermined volume of the liquid sample.

The substances which are employed in the above-described first and second methods to give an indication of the target substance includes a labelled substance which is a substance capable of specifically binding to the target substance in the liquid sample and having a distinguishable labelling agent bound thereto, as well as a substance capable of generating a distinguishable signal such as color development through a reaction between the target substance in the liquid sample.

Typical of the distinguishable labelling agents to be bound to the substance capable of specifically binding to the target substance in the liquid sample are dyes, isotopes, enzymes, and fluorescent materials. Preferred are the enzymes for their stability, detection sensitivity, safety and convenience of handling, and the like. The enzymes which may be utilized in the present process include enzymes which are generally employed in enzyme immunoassays such as horseradish peroxidase and alkaline phosphatase.

The results of the reaction may be obtained by measuring the quantity or the activity of the labelled substance which has been bound to the target substance on the reaction area after the completion of the immunoreaction. When the distinguishable labelling agent is an enzyme, the measurement of the enzyme may be conveniently carried out by measuring the quantity of the substance generated through an enzymatic reaction of the labelling enzyme. The measurement of the substances may be carried out physically and quantitatively be means of devices including reflectance spectrophotometer, fluorophotometer, and emission spectrophotometer. When the distinguishable agent is a coloring reagent, the measurement may be carried out semiquantitatively by dividing the level of color developed in accordance with the strength of the color, or alternatively, by qualitatively determining the positive/negative results, which is more convenient. When the distinguishable labelling agent is an isotope, the measurement may be carried out by a direct measurement of the radioactivity of the isotope.

The coloring reagents whose color is developed by enzymatic reactions may be any reagents which are generally employed in enzyme immunoassays. For example, peroxidase may be detected by using 2,2'-adinodi(3-ethylbenzthiazoline)-6'-sulfonic acid (ABTS), o-phenylenediamine (OPD), tetramethylbenzidine (TMB), 5-aminosalicylic acid, and the like, and alkaline phosphatase may be detected by using the substrate such as p-nitrophenolphosphoric acid or phenylphosphoric acid to detect the color of phenol produced by the enzymatic reaction through oxidative conjugation with 4-aminoantipyrine. Coloring reagents which are likely to be deposited on the solid phase and whose color is less likely to be changed with the lapse of time are more preferable since the results may be maintained after the determination of the results. Many such reagents are known and typical of such coloring reagents are diaminobenzidine for peroxidase and 5-bromo-4-chloro-3-indolylphosphate (BCIP) for alkaline phosphatase.

Typical substance capable of generating a distinguishable signal such as color development through a reaction between the target substance in the liquid sample is, for example, an enzyme in the case wherein the target substance in the liquid sample is a substrate for the enzyme.

The results of the reaction may be obtained by measuring the activity caused by the reaction which had occurred between the target substance on the reaction area. When the target substance in the liquid sample is a substance which is a substrate for a certain enzyme, and the substance capable of generating a distinguishable signal is an enzyme, the measurement may be conveniently carried out by measuring the amount of the substance resulting from the enzymatic reaction. The measurement may be carried out as described for the labelling agents.

Typical combination of the target substance and the enzyme therefor employed in such processes include, $\beta$-D-glucose, which is the target substance, and glucose oxidase, which is the enzyme corresponding to the target substrate; hydrogen peroxide and peroxidase; urea and urease; cholesterol and cholesterol oxidase; cholesterol ester and cholesterol esterase; oxaloacetic acid and malate dehydrogenase; and lactic acid and lactate dehydrogenase.

In the process according to the present invention, once a substantially predetermined volume of the liquid sample has been applied to the reaction area through the porous portion of the porous member, the subsequent steps may not necessarily be carried out immediately after the application of the liquid sample. The samples may be left as they are once a predetermined volume of the liquid sample has been applied and the liquid sample has dried and solidified, and the subsequent steps may be carried out after a sufficient number of the samples have been collected.

Next, a device for measuring a target substance in a liquid sample, which is the second aspect of the present invention, is described in detail.

The device in accordance with the present invention is characterized in that the device is capable of collecting a allows for a convenient in situ measurement of the quantity of the target substance in the liquid sample to be carried out.

The present device is hereinafter described with reference to the drawings.

Figure 2A:
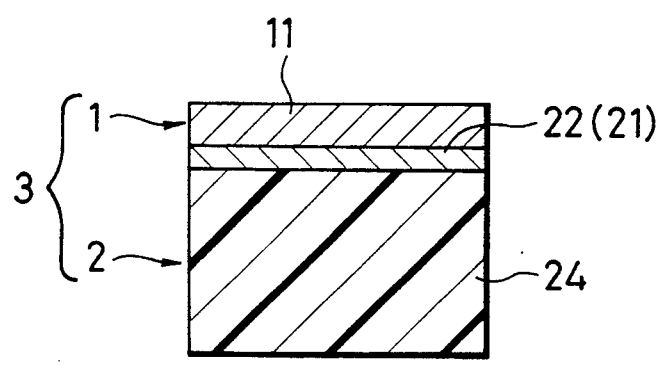
FIGS. 2a and 2b are cross sections of preferred embodiments of the devices according to the present invention.
Figure 2B:
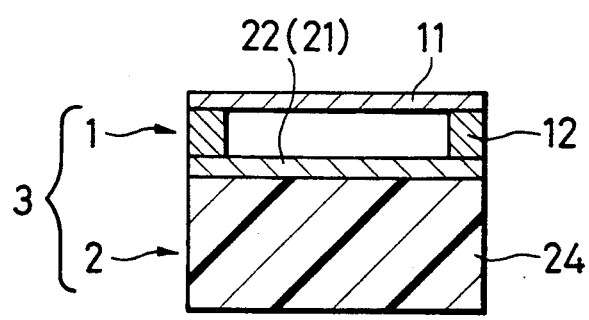
Figure 3A:
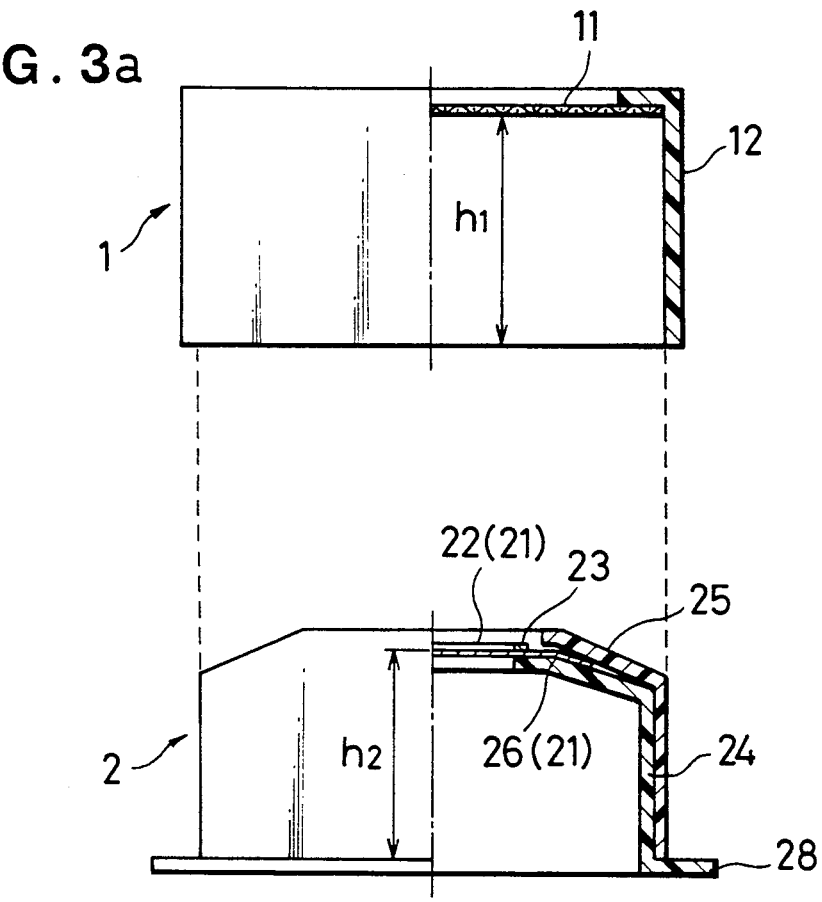
FIG. 3a is a set of partially exploded cross sections of members of another preferred embodiment according to the present invention.

Referring to FIGS. 2a, 2b, 3a, and 3b, a device 3 according to the present invention comprises a porous member 1 and body 2. The porous member 1 is disposed on or above the body 2. portion 11 as shown in FIG. 2a, or comprise the porous portion 11 and a supporting member 12 as shown in FIGS. 2b and 3a.

The porous portion 11 may be formed of a material permitting the liquid sample to be permeated therethrough. Non-limiting examples of such materials include glass fiber filter paper, cellulose filter paper, Nylon net, urethane foam, and synthetic fiber fabric.

A supporting member 12 over which the porous portion 11 is stretched may be formed of non-limiting materials including polyethylene and polyester.

The porous member 1 is not limited to a particular configuration although it may preferably have the same cross section as the body 2 of the device which will be described later. The size of the porous member 1 is also determined in relation to the size of the body 2 of the device which will be described later.

The body 2 of the device has a reaction area 22 comprising a solid phase 21. The size of the porous portion 11 of the porous member 1 may preferably be similar to that of the reaction area 22 of the body 2 of the device.

The body 2 of the device is not limited to a particular configuration although it may preferably have circular, ellipsoidal, quadrilateral, or hexagonal cross section.

Figure 3B:
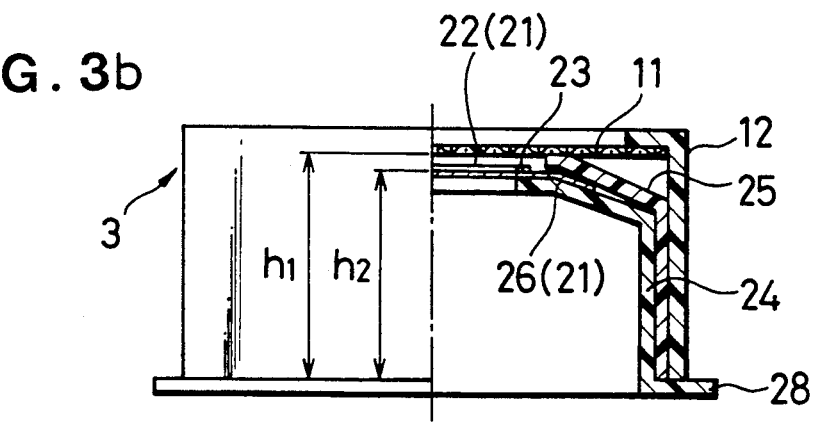
FIG. 3b is a partially sectional side view of the members of FIG. 3a assembled together according to the present invention.

The body 2 of the device may preferably comprise a base 24 over which the sheet-like solid phase 21 is stretched as shown in FIGS. 2a and 2b. The body 2 of the device may preferably further comprise a frame member 25 surrounding the base 24 to fixedly secure the sheet-like solid phase 21 over the base 24 as shown in FIGS. 3a and 3b. The frame member 25 may more preferably comprise a structure capable of stretching the porous portion 11 of the porous member 1 tight and maintaining the distance between the reaction area 22 and the porous portion 11 of the porous member 1 equal all over the area as shown in FIG. 3b.

The base 24 may preferably have an opening to allow for a light to pass therethrough and the sheet-like solid phase 21 may preferably be disposed across the opening so that the measurement may be carried out by making use of the light passing therethrough.

The base 24 and the frame member 25 of the body 2 of the device may preferably comprise various plastic resins such as polyethylene and polyester.

The reaction area 22 may comprise whole area of the solid phase 21. More preferably, the reaction area 22 may comprise a portion of the solid phase 21, and a boundary member 23 may be provided to define a non-reaction area 26 from the reaction area 22 as shown in FIG. 3a. The boundary member 23 is also effective for consistently tightening the sheet-like solid phase within the reaction area 22. The reaction area 22 may also be defined by treating a portion of the solid phase 21 corresponding to the non-reaction area 26 with a water repellent as shown in FIG. 1a.

The non-limiting configurations of the reaction area 22 include circle and ellipsoid.

The solid phase 21 of the body 2 of the device on which the reaction area 22 is provided may preferably comprise a substantially liquid non-permeable sheet-like solid phase.

The solid phase 21 may be made of plastic resins such as polyester, polypropylene, vinyl chloride, polyethylene, polymethylpentene, synthetic membranes such as Nylon and nitro cellulose membranes, and papers coated with afore-mentioned materials. Among these, plastic resins such as polyester, polypropylene, polyethylene, and Nylon membrane are preferable since they are easy to wash and convenient to handle. In particular, when the liquid sample is nipple discharge and the target substance to be measured is CEA, the solid phase 21 may preferably comprise plastic resins including polyester, polypropylene, and polyethylene, and Nylon membrane to minimize non-specific adsorption.

The sheet-like solid phase 21 may preferably be liquid-nonpermeable to maintain the accuracy of the volume of the sample involved in the reaction even when an extremely minute sample is collected and to minimize the effects on the measurements of the properties of the liquid sample such as viscosity.

Moreover, when the sheet-like solid phase 21 is substantially liquid-nonpermeable, components which failed to adsorb on the reaction area 22 comprising such solid phase may be readily removed by washing either before or after the drying of the sample irrespective of the viscosity of the sample. Consequently, the effects on the measurements of the drying of the sample or the properties of the sample may be greatly minimized.

This is quite convenient for such a scene as mass screening wherein a large number of samples are occasionally collected. In such a case, the samples may be left as they are after the application of the sample onto the reaction area 22 through the porous portion 11 of the porous member 1, and subsequent steps may be carried out after a sufficient number of the samples have been collected.

The afore-mentioned advantages are particularly significant when the sheet-like solid phase is made from a substantially liquid-nonpermeable plastic resin.

As mentioned above, the solid phase may comprise the reaction area 22 and the non-reaction area 26. The boundary member 23 defining the former from the latter may be provided on the solid phase 21 by such means as printing, vapor deposition, and thermocompression bonding using such material as epoxy resin. Provision of such a boundary member 23 may also result in consistent tightening of the reaction area 22, which results in improved accuracy of the volume of the liquid sample collected.

The non-reaction area 26 may also be provided by treating a portion of the solid phase 21 with such material as water repellent. Exemplary materials which may be used in such treatment include water repellents such as silicone and epoxy resins and metals such as aluminum.

Onto at least a portion of the solid phase 21, there may be immobilized a substance which is reactive with or which binds to the target substance to be measured in the liquid sample to provide the reaction area 22. The term immobilization used herein means that a reactive substance or a binding substance is bound to the solid phase 21 by such means as chemical or physical bond such that it would not be substantially released during the reaction. The sensitivity of the measurement is improved by such immobilization of the reactive or binding substance.

The substance which is reactive with or which binds to the target substance to be measured in the liquid sample which is immobilized onto at least a portion of the solid phase 21 may be the one described for the first aspect of the present invention.

The immobilization of the substance which is reactive or which binds to the target substance to be measured in the liquid sample onto the entire solid phase 21 may be carried out as described below when the substance which binds to the target substance to be measured in the liquid sample is, for example, an antibody.

The antibody may be either a commercially available one or one prepared by a conventional method.

The antibody may be immobilized onto the reaction area comprising the solid phase either physically or chemically. For example, the solid phase is immersed in a solution of the antibody, and incubated at 4° to 56° C. for 0.5 to 24 hours, preferably at 37° to 50° C. for 1 to 2 hours to physically immobilize the antibody onto the reaction area.

When the antibody is a purified antibody or a purified antibody fragment, the concentration of the antibody employed may be 1 μg to 100 mg/mL, and preferably 1 to 100 μg/mL.

The solid phase immersed in the antibody solution may be dried either by air-drying or lyophilization.

The immobilization of an antibody onto the reaction area comprising the solid phase is not limited to the above-described method. The immobilization may be carried out by any method wherein the antibody is immobilized onto the reaction area such that the antibody would not be substantially released from the reaction area during the application of the sample liquid or labelled substance thereto as well as rinsing operations which are involved in ordinary measurement procedures.

After the immobilization of the antibody onto the reaction area comprising the solid phase, the reaction area may be coated with a substance which does not participate in the antigen-antibody reaction between the target substance in the liquid sample such as cytochrome c solution which has been heated and modified, BSA (bovine serum alubmin), HSA (human serum albumin), animal serum, skimmed milk, and the like to suppress non-specific reactions for easy determination of the results.

The amount of the antibody immobilized onto the reaction area is determined in relation to the concentration of the target substance to be measured in the liquid sample. For example, in a measurement system wherein a concentration of the target substance in the liquid sample which is higher than the predetermined concentration (cut off concentration) is to be determined as positive, an amount of the antibody just sufficient for all the antigen-binding sites of the antibodies immobilized within the reaction area to be substantially saturated by the target substance at the cut off concentration may be immobilized on the reaction area for an easy and accurate determination. In another example, when the target substance in the liquid sample is to be quantitatively or semi-quantitatively determined at a predetermined range of concentration, an amount of the antibody such that all the antigen-binding sites of the antibodies immobilized on the reaction area would be substantially saturated by the target substance at the upper limit of the predetermined concentration range may be immobilized on the reaction area for an easy and accurate determination.

The device 3 in accordance with the present invention comprises critical components of the porous member 1 and the body 2. The porous member 1 is disposed in relation to the body 2 as described below.

The porous portion 11 of the porous member 1 may be disposed either in direct contact with the reaction area 22 of the body 2 as shown in FIG. 2a, or at a predetermined distance from the reaction area 22 of the body 2 as shown in FIGS. 2b and 3b. The position of the porous member 1 in relation to the body 2 is selected in accordance with the material employed for the porous portion 11 of the porous member 1 and the properties such as viscosity of the sample to be measured.

Referring to FIG. 3b, the body 2 of the device 3 has a flange 28, and the height $h_1$ between the upper surface of the flange 28 and the porous portion 11 of the porous member 1 is larger than the height $h_2$ between the upper surface of the flange 28 and the upper surface of the reaction area 22 of the body 2. The distance between the porous portion 11 and the reaction area 22 is maintained at a predetermined value all over the reaction area 22 since the porous portion 11 of the porous member 1 is stretched tight by the frame member 25 of the body 2.

The structures for providing a space between the porous portion 11 of the porous member 1 and the reaction area 22 of the body 2 are not limited to those described in FIGS. 2b and 3b. For example, a structure similar to that of FIG. 3b except that the supporting member 12 does not reach the upper surface of the flange 28 of the body 2 is also suitable for a device of the present invention.

The porous member 1 may be either fixedly secured to the body 2 or removably mounted on the body 2 of the device.

The device 3 of the present invention comprises the critical components of the porous member 1 and the body 2 as described above. The device 3, however, may preferably further comprise a remover 41.

As shown in FIGS. 1b through 1c, the remover 41 is used to remove the excess portion of the liquid sample 40 remaining on the porous portion 11 after the application of the liquid sample 40 onto the porous portion 11 of the porous member 1. Also, the remover 41 may be used to remove the excess portion of the reaction solution.

The remover 41 may be a spatula when the liquid sample 40 is viscous. Preferably, the remover 41 may be made of a liquid-absorbable material which is capable of absorbing excess liquid sample 40, such as porous polyethylene, polyurethane, filter paper, and fabric.

The device of the present invention has been set forth above in accordance with some embodiments of the invention. The device of the present invention is further described in accordance with further embodiments of the present invention. The device of the present invention is provided with at least one reaction area on the body of the device wherein the sample is measured.

Figure 4A:
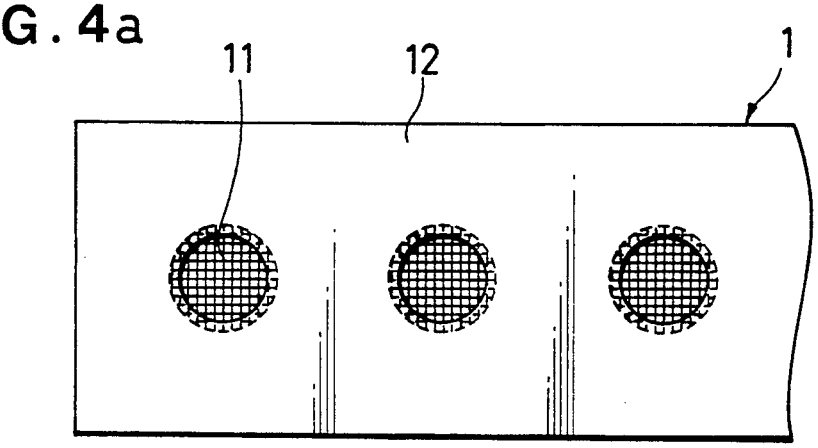
FIGS. 4a and 4b are exploded plan views of members of still another preferred embodiment according to the present invention.
Figure 4B:
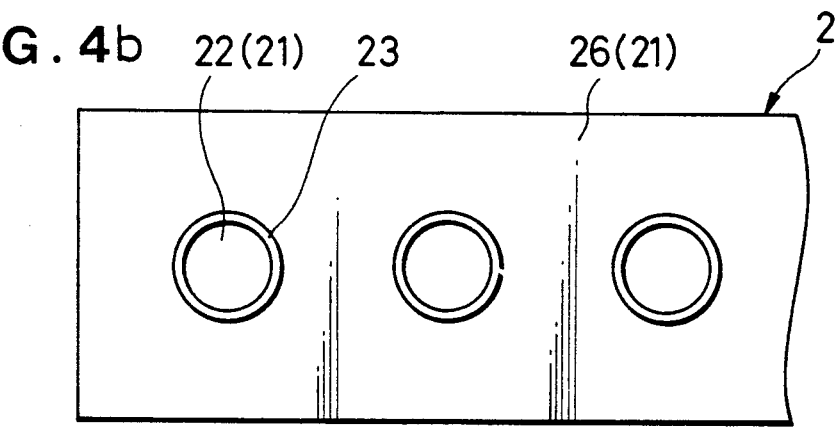
Figure 4C:
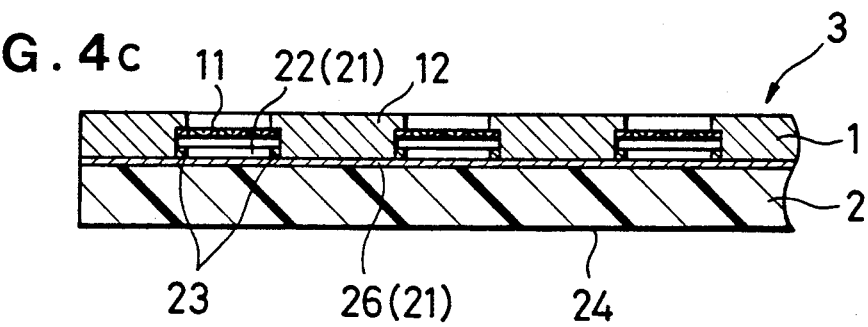
FIG. 4c is a partially sectional side view illustrating the members of FIGS. 4a and 4b assembled together in accordance with the present invention.

Referring to FIGS. 4a, 4b, and 4c, a preferred embodiment of the device 3 in accordance with the present invention is shown, wherein a plurality of reaction areas 22 defined by the boundary members 23 are provided.

FIG. 4a is a plan view of the porous member 1. FIG. 4b is a plan view of the body 2. FIG. 4c is a cross section of the device 3 comprising the assembly of the porous member 1 and the body 2.

In this embodiment, the porous portion 1 may be either fixedly secured to the body 2 of the device or removably mounted on the body 2 of the device. The supporting member 12 of the porous member 1 is disposed on the non-reaction area 26 of the body 2 to define a space between the porous portion 11 and the reaction area 22 wherein the distance therebetween is equal all over the reaction area 22. The predetermined volume of the liquid sample is collected in this space.

In this embodiment, each of the porous portion 11 of the porous member 1 corresponds to each of the reaction area 22 of the body 2 of the device. A structure wherein the body 2 of the device provided with a plurality of the reaction areas 22 is covered by one large porous portion may also be preferable.

In such embodiments wherein a plurality of the reaction areas 22 are provided on the body 2, a plurality of different samples may be reacted at the same time, and this is particularly advantageous for such scene as mass screening.

Preferably, the device of the present invention may further comprise reaction areas for contrast and/or standard substance.

Figure 6A:
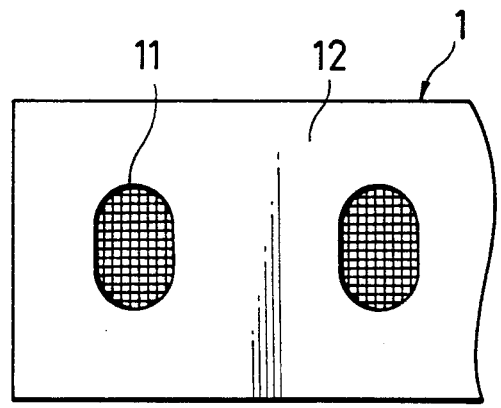
FIGS. 6a and 6b are exploded plan views of members of still further preferred embodiment having a reaction area for contrast according to the present invention.
Figure 6B:
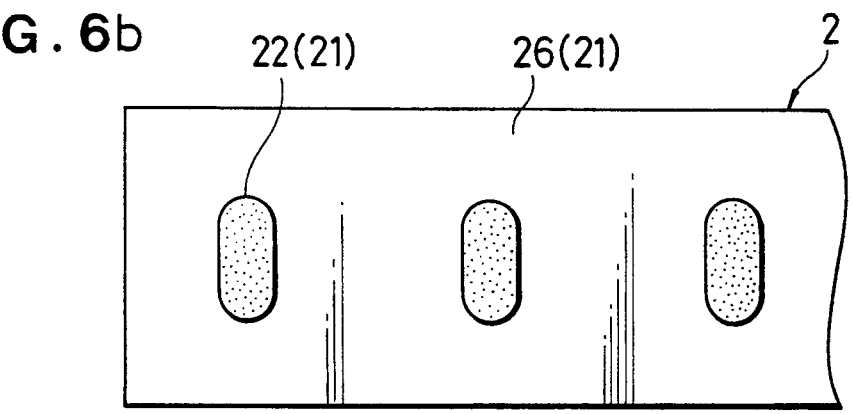
Figure 6C:
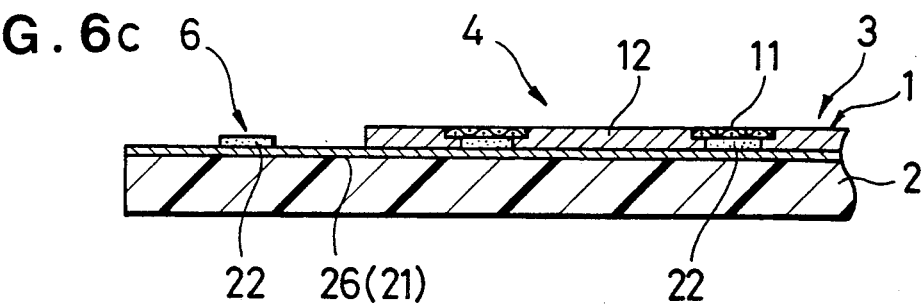
FIG. 6c is a partially sectional side view of the members of FIGS. 6a and 6b assembled together in accordance with the present invention.

Referring to FIGS. 6a, 6b, and 6c, there are illustrated a further preferred embodiment of the device 3 in accordance with the present invention. In this embodiment, the device 3 has a reaction area for contrast 6 having immobilized thereto a substance which is reactive or which binds to a substance which is non-reactive with the target substance to be measured in the liquid sample as well as a sample-measuring portion 4 comprising a plurality of sample reaction areas 22 having immobilized thereto a substance which is reactive with or which binds to the target substance to be measured in the liquid sample.

FIG. 6a is a plan view of the porous member 1. FIG. 6b is a plan view of the body 2. FIG. 6c is a cross section of the device 3 comprising the assembly of the porous member 1 and the body 2.

As shown in FIG. 6c, each of the reaction area 22 of the sample measuring portion 4 is covered with each of the porous portion 11 of the porous member 1 whereas the contrast reaction area 6 is not covered with the porous member 1.

In this embodiment, the porous portion 1 may be either fixedly secured to the body 2 of the device or removably mounted on the body 2 of the device.

The supporting member 12 of the porous member 1 is disposed on the non-reaction area 26 of the solid phase 21 of the body 2, and the porous portion 11 is substantially in contact with the reaction area 22. The predetermined volume of the liquid sample is collected within the porous portion 11 or between the porous portion 11 and reaction area 22.

The contrast reaction area 6 enables to confirm whether the rinsing has been sufficiently carried out or not. The contrast reaction area 6 also increases accuracy of the qualitative determination of the sample.

Referring to FIG. 5, there is illustrated an embodiment wherein a standard measuring portion 5 is included to carry out reactions of a plurality of standard samples having different concentrations thereon as well as the sample measuring portion 4 comprising the porous member 1 and the body 2.

In this embodiment, the standard measuring portion 5 includes a plurality of the reaction areas 22 comprising the solid phase 21, and is not covered by the porous member 1. The reaction area 22 and the non-reaction area 26 of the standard measuring portion 5 may be defined by providing the boundary member 23, by treating the non-reaction area with a water repellent, or by immobilizing a substance which is reactive or which binds to the target substance to be measured onto only the reaction area 22, as in the case of the sample measuring portion 4.

The device as shown in FIG. 5 allows for a quantitative, semi-quantitative, or qualitative measurement of the target substance in the liquid sample to be readily and accurately carried out, since the sample and the standard may be simultaneously reacted thereon.

For the purpose of giving those skilled in the art a better understanding of the present invention, the following illustrative, non-limiting examples are given.

EXAMPLES

EXAMPLE 1

This example illustrates the volume of the liquid samples collected by using various materials for the porous portion of the porous member in the measuring device in accordance with the present invention.

The measuring devices were prepared, and the liquid samples were collected by using the measuring device to determine the volume of the liquid samples collected as set forth below. The results are shown in Tables 1-i) through 1-vi).

(a) Preparation of the measuring device

Single or double layered disk having a diameter of 6 mm made of the filter paper or the Nylon net as listed below, which constitutes the porous portion of the porous member, was disposed above a 1 mm thick polyethylene disk having a diameter of 6 mm. The distance between the porous disk and the polyethylene disk was kept at 0.04 mm.

| i) glass fiber filter paper single layered | |
|---|---|
| thickness | 0.4 mm |
| pore size | 1 μm |
| ii) cellulose filter paper single layered | |
| thickness | 0.2 mm |
| pore size | 1 μm |
| iii) Nylon net single layered | |
| pore size | 10 μm |
| iv) Nylon net single layered | |
| pore size | 20 μm |
| v) Nylon net single layered | |
| pore size | 30 μm |
| vi) Nylon net double layered | |
| pore size | 30 μm |

(b) Collection of the liquid sample

Onto the filter paper or the Nylon net of the measuring device whose weight had been previously measured, 5 μL of the liquid sample, which was distilled water, urine, serum, or nipple discharge, was applied. The liquid sample remaining on the filter paper or the Nylon net was subsequently absorbed by bringing a cellulose paper having the pore size of 50 μm in contact with the upper surface of the filter paper or the Nylon net to remove excess volume of the liquid sample.

Weight of the device was then measured without delay, and the measurement was corrected by specific gravity of each sample to obtain the volume of the liquid sample collected by the device. The above described measurement was repeated 10 times for each type of the liquid sample.

TABLE 1-i

Single-layered glass fiber filter paper having the pore size of 1 μm.

| | Volume of liquid sample collected, μL | | | |
|---|---|---|---|---|
| run | distilled water | urine | serum | nipple discharge |
| 1 | 3.95 | 4.10 | 4.02 | 4.32 |
| 2 | 4.21 | 4.32 | 4.17 | 4.67 |
| 3 | 4.20 | 4.27 | 3.80 | 4.03 |
| 4 | 4.06 | 4.14 | 3.99 | 4.19 |
| 5 | 4.18 | 3.77 | 4.37 | 3.96 |
| 6 | 4.33 | 4.45 | 3.98 | 4.56 |
| 7 | 4.07 | 4.01 | 4.25 | 4.01 |
| 8 | 3.99 | 4.46 | 4.39 | 4.38 |
| 9 | 4.36 | 4.36 | 4.00 | 3.85 |
| 10 | 4.18 | 3.97 | 4.01 | 4.54 |
| Average | 4.15 | 4.19 | 4.10 | 4.25 |
| C.V. | 3.3% | 5.3% | 4.6% | 6.7% |

TABLE 1-ii

Single-layered cellulose filter paper having the pore size of 1 μm.

| | Volume of liquid sample collected, μL | | | |
|---|---|---|---|---|
| run | distilled water | urine | serum | nipple discharge |
| 1 | 1.84 | 1.69 | 1.75 | 1.94 |
| 2 | 1.62 | 1.71 | 1.84 | 1.97 |
| 3 | 1.63 | 1.94 | 1.71 | 1.61 |
| 4 | 1.69 | 1.88 | 1.98 | 1.78 |
| 5 | 1.97 | 1.81 | 1.96 | 1.78 |
| 6 | 1.72 | 1.76 | 1.69 | 1.66 |
| 7 | 1.81 | 1.92 | 1.74 | 1.82 |
| 8 | 1.95 | 1.77 | 1.83 | 1.85 |
| 9 | 1.95 | 1.79 | 1.87 | 1.85 |
| 10 | 1.78 | 1.93 | 1.68 | 1.69 |
| Average | 1.80 | 1.82 | 1.81 | 1.80 |

TABLE 1-ii-continued

Single-layered cellulose filter paper having the pore size of 1 μm.

| | Volume of liquid sample collected, μL | | | |
|---|---|---|---|---|
| run | distilled water | urine | serum | nipple discharge |
| C.V. | 7.3% | 5.1% | 6.0% | 6.5% |

TABLE 1-iii

Single-layered Nylon net having the pore size of 10 μm.

| | Volume of liquid sample collected, μL | | | |
|---|---|---|---|---|
| run | distilled water | urine | serum | nipple discharge |
| 1 | 0.15 | 0.13 | 0.15 | 0.16 |
| 2 | 0.17 | 0.12 | 0.13 | 0.14 |
| 3 | 0.14 | 0.13 | 0.14 | 0.13 |
| 4 | 0.14 | 0.15 | 0.14 | 0.16 |
| 5 | 0.14 | 0.14 | 0.15 | 0.15 |
| 6 | 0.13 | 0.16 | 0.12 | 0.14 |
| 7 | 0.15 | 0.15 | 0.14 | 0.15 |
| 8 | 0.14 | 0.13 | 0.13 | 0.17 |
| 9 | 0.13 | 0.14 | 0.16 | 0.16 |
| 10 | 0.13 | 0.16 | 0.14 | 0.17 |
| Average | 0.14 | 0.14 | 0.14 | 0.15 |
| C.V. | 8.7% | 9.7% | 8.2% | 8.7% |

TABLE 1-iv

Single-layered Nylon net having the pore size of 20 μm.

| | Volume of liquid sample collected, μL | | | |
|---|---|---|---|---|
| run | distilled water | urine | serum | nipple discharge |
| 1 | 0.51 | 0.42 | 0.43 | 0.44 |
| 2 | 0.46 | 0.48 | 0.49 | 0.52 |
| 3 | 0.52 | 0.50 | 0.46 | 0.48 |
| 4 | 0.49 | 0.47 | 0.45 | 0.46 |
| 5 | 0.48 | 0.45 | 0.46 | 0.49 |
| 6 | 0.48 | 0.46 | 0.47 | 0.47 |
| 7 | 0.47 | 0.44 | 0.48 | 0.45 |
| 8 | 0.45 | 0.49 | 0.47 | 0.50 |
| 9 | 0.50 | 0.42 | 0.43 | 0.46 |
| 10 | 0.53 | 0.44 | 0.49 | 0.47 |
| Average | 0.49 | 0.46 | 0.46 | 0.47 |
| C.V. | 5.3% | 6.1% | 4.7% | 5.1% |

TABLE 1-v

Single-layered Nylon net having the pore size of 30 μm.

| | Volume of liquid sample collected, μL | | | |
|---|---|---|---|---|
| run | distilled water | urine | serum | nipple discharge |
| 1 | 0.72 | 0.72 | 0.84 | 0.91 |
| 2 | 0.71 | 0.74 | 0.89 | 0.87 |
| 3 | 0.81 | 0.80 | 0.73 | 0.91 |
| 4 | 0.80 | 0.81 | 0.72 | 0.89 |
| 5 | 0.77 | 0.80 | 0.73 | 0.81 |
| 6 | 0.69 | 0.78 | 0.81 | 0.86 |
| 7 | 0.84 | 0.73 | 0.77 | 0.80 |
| 8 | 0.72 | 0.69 | 0.85 | 0.85 |
| 9 | 0.76 | 0.74 | 0.70 | 0.85 |
| 10 | 0.78 | 0.73 | 0.80 | 0.78 |
| Average | 0.76 | 0.75 | 0.78 | 0.85 |
| C.V. | 6.4% | 5.4% | 8.2% | 5.3% |

Table 1-vi

Double-layered Nylon net having the pore size of 30 μm.

| | Volume of liquid sample collected, μL | | | |
|---|---|---|---|---|
| run | distilled water | urine | serum | nipple discharge |
| 1 | 1.27 | 1.17 | 1.19 | 1.22 |
| 2 | 1.16 | 1.25 | 1.19 | 1.19 |
| 3 | 1.22 | 1.31 | 1.24 | 1.15 |
| 4 | 1.24 | 1.24 | 1.29 | 1.28 |
| 5 | 1.20 | 1.22 | 1.29 | 1.27 |
| 6 | 1.13 | 1.25 | 1.31 | 1.16 |
| 7 | 1.24 | 1.16 | 1.24 | 1.20 |
| 8 | 1.19 | 1.22 | 1.23 | 1.18 |
| 9 | 1.29 | 1.23 | 1.21 | 1.19 |
| 10 | 1.24 | 1.24 | 1.23 | 1.27 |
| Average | 1.22 | 1.23 | 1.24 | 1.21 |
| C.V. | 4.0% | 3.4% | 3.4% | 3.9% |

EXAMPLE 2

This example illustrates the volume of the liquid samples collected when different volumes of the liquid samples are applied to the measuring device of the present invention.

The measuring device was prepared in accordance with Example 1-v), and the weight of the device was measured. Onto the Nylon net of the device, 1, 2, 5, 10, or 10 μL of serum was applied, and the serum remaining on upper surface of the net was absorbed by a cellulose filter paper having the pore size of 50 μm to remove excess volume of the serum.

Weight of the device was then measured without delay, and the measurement was corrected by specific gravity of each sample to obtain the volume of the serum collected by the device. The above described measurement was repeated 10 times. The results are shown in Table 2.

Table 2

| | Volume of serum collected, μL | | | | |
|---|---|---|---|---|---|
| | Volume of serum added, μL | | | | |
| run | 1 | 2 | 5 | 10 | 20 |
| 1 | 0.77 | 0.67 | 0.64 | 0.73 | 0.72 |
| 2 | 0.66 | 0.75 | 0.69 | 0.68 | 0.69 |
| 3 | 0.72 | 0.91 | 0.74 | 0.69 | 0.65 |
| 4 | 0.74 | 0.74 | 0.62 | 0.82 | 0.78 |
| 5 | 0.70 | 0.72 | 0.79 | 0.73 | 0.77 |
| 6 | 0.63 | 0.75 | 0.81 | 0.66 | 0.66 |
| 7 | 0.74 | 0.66 | 0.74 | 0.68 | 0.70 |
| 8 | 0.74 | 0.72 | 0.73 | 0.65 | 0.68 |
| 9 | 0.69 | 0.73 | 0.71 | 0.79 | 0.69 |
| 10 | 0.79 | 0.74 | 0.73 | 0.60 | 0.77 |
| Average | 0.72 | 0.74 | 0.72 | 0.70 | 0.71 |
| C.V. | 6.8% | 9.2% | 8.2% | 9.4% | 6.6% |

EXAMPLE 3

This example illustrates effects of the type of the material used for the porous portion of the porous member on reactivity of the enzymatic reaction.

A predetermined amount of horseradish peroxidase (hereinafter abbreviated as HRPO) was insolubilized onto the polyethylene disks of the devices of Example 1. The enzymatic reaction was carried out as described below, and absorbance at 492 nm of the reaction solution was measured.

The measurement was repeated 10 times for each device. The results are shown in Table 3.

Enzymatic reaction

On to the filter paper or the Nylon net of the device, 5 μL of McIlvain buffer solution containing 3 mg/mL of o-phenylene diamine and 0.01% hydrogen peroxide were applied, and the reaction solution remaining on the filter paper or the net was absorbed by bringing a nitrocellulose filter paper having the pore size of 50 μm into contact with the upper surface of the filter paper or the net to remove excess volume of the reaction solution.

The reaction was promoted at room temperature for 30 minutes, 50 μL of 1 M phosphate solution were added dropwise onto the filter paper or the Nylon net, and the filter paper or the net was subsequently removed.

Table 3

| | Absorbance Porous Member | | | | | |
|---|---|---|---|---|---|---|
| run | i | ii | iii | iv | v | vi |
| 1 | 1.980 | 0.730 | 0.066 | 0.209 | 0.438 | 0.718 |
| 2 | 1.755 | 0.742 | 0.075 | 0.212 | 0.393 | 0.651 |
| 3 | 1.826 | 0.874 | 0.082 | 0.248 | 0.429 | 0.676 |
| 4 | 1.668 | 0.903 | 0.079 | 0.230 | 0.397 | 0.680 |
| 5 | 1.594 | 0.728 | 0.081 | 0.241 | 0.401 | 0.656 |
| 6 | 1.724 | 0.759 | 0.068 | 0.217 | 0.450 | 0.660 |
| 7 | 1.870 | 0.814 | 0.069 | 0.250 | 0.448 | 0.674 |
| 8 | 1.843 | 0.881 | 0.070 | 0.204 | 0.415 | 0.702 |
| 9 | 1.852 | 0.746 | 0.074 | 0.196 | 0.403 | 0.705 |
| 10 | 1.717 | 0.825 | 0.073 | 0.205 | 0.456 | 0.643 |
| Average | 1.783 | 0.800 | 0.074 | 0.221 | 0.423 | 0.677 |
| C.V. | 6.3% | 8.5% | 7.6% | 8.9% | 5.7% | 3.7% |

EXAMPLE 4

This sample illustrates effects on accuracy of the measurements of the removal of excess volume of the liquid sample on the porous portion of the present device.

The measuring device was prepared as described below, and the liquid sample was collected by using the thus prepared device. Excess volume of the liquid sample was either removed or not removed, and CEA concentration of the liquid sample was subsequently measured. The results are shown in Tables 4-i) through iii).

(a) Preparation of the measuring device

A circle having the inner diameter of 10 mm was printed on a surface of ground glass with a coating containing Teflon. Anti-CEA antibody was insolubilized on the ground glass within the printed circle. A disk having the diameter of 10 mm made of single layered Nylon net having the pore size of 30 μm was fixedly secured above the circle at a distance of 0.04 mm from the ground glass.

(b) Collection of the liquid sample

Onto the Nylon net of the device, 1 to 5 μL of the liquid samples (i) urine, ii) serum and iii) nipple discharge) having added thereto an authentic sample of CEA to the CEA concentration of 10 ng/mL were applied. Either with or without removal of excess volume of the liquid sample by bringing a nitrocellulose filter paper having the pore size of 50 μm into contact with upper surface of the Nylon net to absorb the excess liquid sample, the enzymatic reaction as described below was subsequently carried out.

(c) Enzymatic reaction

To the Nylon net of the device, 25 μL of solution containing anti-CEA antibody labeled with HRPO were added dropwise and the reaction was promoted at room temperature for 60 minutes.

The net was removed, and unreacted HRPO-labeled antibody was removed by washing with 0.1 M phosphate buffered saline having 0.05% Tween 20 added thereto.

After removing the excess fluid with filter paper, 50 μL of McIlvain buffer solution containing 3 mg/mL of phenylene diamine and 0.01% hydrogen peroxide were added dropwise to the reaction surface, and the reaction was carried out at room temperature for 60 minutes.

50 μL of 1 M phosphate solution were added dropwise, agitated, and absorbance at 660 nm of the reaction solution was measured.

TABLE 4-i

| Volume of liquid sample, μL | Urine Measurement, ng/mL | | | |
|---|---|---|---|---|
| | without removal | | with removal | |
| 1 | 10.1 | 10.5 | 11.0 | 9.1 |
| 2 | 9.5 | 11.0 | 9.5 | 9.4 |
| 3 | 13.0 | 11.7 | 8.9 | 10.3 |
| 4 | 10.8 | 9.9 | 10.5 | 9.8 |
| 5 | 12.7 | 10.0 | 10.2 | 10.6 |
| Average | 10.9 | | 9.9 | |
| C.V. | 11.0% | | 7.0% | |

Table 4-ii

| Volume of liquid sample, μL | Serum Measurement, ng/mL | | | |
|---|---|---|---|---|
| | without removal | | with removal | |
| 1 | 11.4 | 12.1 | 10.0 | 9.8 |
| 2 | 9.8 | 10.9 | 9.6 | 8.8 |
| 3 | 10.5 | 12.3 | 11.1 | 10.3 |
| 4 | 12.0 | 10.2 | 10.0 | 10.3 |
| 5 | 9.9 | 10.4 | 9.4 | 10.5 |
| Average | 11.0 | | 10.0 | |
| C.V. | 8.6% | | 6.3% | |

TABLE 4-iii

| Volume of liquid sample, μL | Nipple discharge Measurement, ng/mL | | | |
|---|---|---|---|---|
| | without removal | | with removal | |
| 1 | 11.7 | 10.5 | 9.7 | 10.6 |
| 2 | 13.1 | 12.8 | 10.3 | 10.4 |
| 3 | 11.9 | 10.0 | 11.7 | 10.2 |
| 4 | 12.3 | 12.4 | 10.9 | 10.2 |
| 5 | 10.6 | 10.5 | 9.7 | 10.9 |
| Average | 11.6 | | 10.5 | |
| C.V. | 9.5% | | 5.8% | |

EXAMPLE 5

In this example, CEA concentration measured with the device of the present invention was compared with CEA concentration measured with a conventional CEA-detection kit.

The measuring device was prepared as described below, nipple discharge was collected by using the thus prepared device, and the CEA concentration of the nipple discharge was measured.

The CEA concentration for the identical nipple discharge was also measured by using Elmotech-CEA (manufactured by Mochida Pharmaceutical Co., Ltd.).

Figure 7:
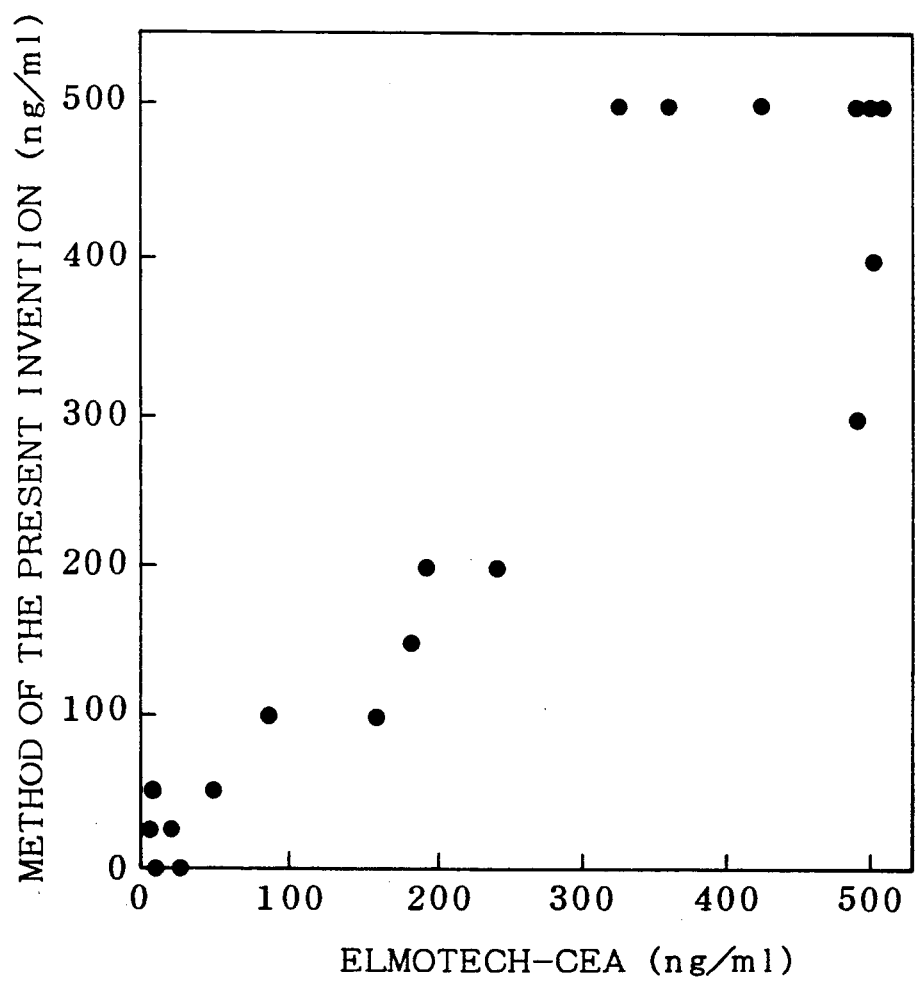
FIG. 7 diagrammatically illustrates CEA concentration of nipple discharge measured by the device of the present invention in relation to the CEA concentration measured by Elmotech-CEA.

The results are shown in FIG. 7.

(a) Preparation of the measuring device

An embossed polyester film of 0.2 mm thick was immersed in 0.1 μg/mL anti-CEA antibody solution, incubated at 4° C. for 24 hours, and washed with distilled water to prepare an antibody-insolubilized film.

A disk having the diameter of 10 mm was cut out of the thus prepared antibody-insolubilized film. The disk was disposed on a base, and fixedly secured by means of a frame member to prepare a body of the device.

A porous member comprising a Nylon net fused on a support member was disposed and secured on the body of the device to assemble the device.

(b) Collection of the liquid sample

The nipple discharge to be measured was collected by directly pressing the net portion of the thus prepared measuring device against outlet of the lactiferous duct secreting the nipple discharge.

A remover made of absorbent porous polyethylene was lightly pushed against the net to remove excess volume of the liquid sample.

Approximately 1 μL of the liquid sample was collected by the above-described procedure.

(c) Enzymatic reaction

Onto the net of the device, 10 μL of anti-CEA antibody solution labelled with HRPO were added dropwise, and the reaction was carried out at room temperature for 30 minutes.

After removing the porous member, unreacted HRPO-labeled antibody was removed by washing with 0.1 M phosphate buffered saline, pH 7.0 having 0.05% Tween 20 added thereto.

After thoroughly removing the excess fluid with filter paper, 10 μL of substrate solution containing 0.5 mM tetramethylbenzidine and 0.01% hydrogen peroxide were added dropwise, and the reaction was carried out at room temperature for 30 minutes.

The above described procedure was repeated for a CEA standard solution having CEA concentration of 0 and 1,000 ng/mL except that no porous member was employed.

Absorbance at 660 nm was measured for both the nipple discharge and the CEA standard solution 30 minutes after the addition of the substrate solution.

CEA concentration of the liquid sample was calculated by using a standard curve prepared from the absorbance of the CEA standard solution. (d) Measurement by conventional detection kit The identical samples were measured for CEA concentration by using Elmotech-CEA (manufactured by Mochida Pharmaceutical Co., Ltd). The measurements were compared with those obtained by using the device of the present method.

Correlation factor was 0.91.

EXAMPLE 6

Nipple discharge samples collected from patients exhibiting abnormal secretion of nipple discharge were measured for their CEA concentration by repeating the procedure of Example 5 using the device of Example 5.

Figure 8:
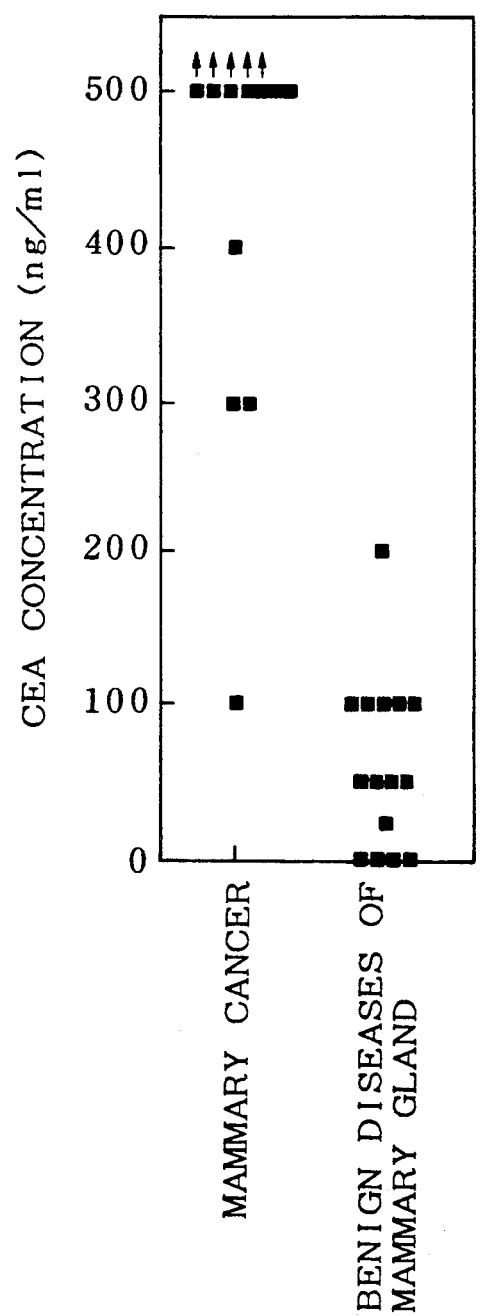
FIG. 8 diagrammatically illustrates CEA concentration of nipple discharges collected from patients suffering from both malignant and benign diseases measured by the device of the present invention.

The results are shown in FIG. 8.

In Example 1, the volume of the liquid sample collected was examined in relation to the type of the material employed for the porous portion of the porous member according to the present invention.

As apparent from Tables 1-i) through 1-vi), a substantially constant volume of the liquid sample can be collected by selecting an appropriate material for the porous portion of the porous member irrespective of the type or the properties of the liquid sample collected. Furthermore, any desired volume of the liquid sample may be collected by appropriately selecting the material for the porous portion of the porous material as illustrated by the different volumes of the liquid samples collected by the different types of the materials of the porous portion employed even when the distance between the porous portion of the porous member and the body of the device was the same.

In Example 2, the volume of the liquid samples collected was examined in relation to the volume of the liquid samples applied. As apparent from Table 2, among the averages of the 5 groups wherein 1, 2, 5, 10 and 20 μL of the liquid samples were applied, no significant difference is recognized at the risk rate of $P<0.05\%$. Therefore, it is apparent that a constant volume of the liquid sample may be applied on the reaction area irrespective of the volume of the liquid sample applied.

Example 3 was carried out to examine effects of the type of the material of the porous portion of the porous member on the reactivity of the enzyme by carrying out an enzymatic reaction using the measuring device of the present process.

The data in Table 3 reveal that the reactivity varied in accordance with the material of the porous member employed even when the distance between the porous portion of the porous member and the reaction area of the body of the device was constant because the volume of the reaction solution applied onto the reaction area would be different depending on the material. Therefore, the reactivity can be varied by appropriately selecting the material for the porous portion of the porous material.

In Example 4, accuracy of the measurements was compared when the present process was carried out with and without the removal of excess volume of the liquid sample.

The data in Tables 4-i) through iii) reveal that the removal of excess volume of the liquid sample would improve the accuracy of the measurement, although the accuracy of the measurement without the removal of the excess liquid sample was allowable irrespective of the type and the properties of the liquid sample.

In Example 5, CEA concentration measured by using the device of the present invention was compared with the CEA concentration measured by using conventional Elmotech-CEA manufactured by Mochida Pharmaceutical Co., Ltd.

Comparison between the measurements obtained by using the device of the present invention and Elmotech-CEA showed a quite good correlation, namely, $Y=0.85X+13.6$ and correlation coefficient of $r=0.91$ (see FIG. 7).

In Example 6, CEA concentration of the nipple discharges collected from patients suffering from abnormal secretion of the nipple discharge were measured by using the device of the present invention, and the thus obtained measurements were compared between benign and malignant diseases.

The measurements were divided into two groups, which were the measurements obtained from patients suffering from mammary cancer and those obtained from patients suffering from benign diseases of mammary gland. The CEA concentration of the nipple discharges collected from the mammary cancer patients exhibited significantly higher value except for one case. This result confirmed high availability of the present process employing the device of the present invention for diagnosing mammary cancer (see FIG. 8).

As described above, a convenient method for measuring a target substance in a liquid sample is provided by the present invention, which is capable of collecting a predetermined volume of the sample even when the volume of the sample is minute. A device used in said method comprising a structure capable of collecting a predetermined volume of the liquid sample is also provided by the present invention.

A convenient method for a quantitative measurement requiring a constant amount of the sample to be applied is also realized by the present invention, which may be used even when the volume of the liquid sample is minute and the properties of the sample is different from sample to sample. A measurement of the target substance contained in such sample as nipple discharge, whose measurement has been difficult if not impossible, was enabled by the present invention.

Further, efficiency of the measurement in such occasion as clinical examination may be markedly increased by the present invention since the present invention is simple to operate. The present invention, therefore, is quite suitable for use in mass screening.

It is to be noted that the present invention has enabled to measure not only concentration but also absolute quantity of the target substance in the liquid sample even when the volume of the sample is minute.

We claim:

1. A device for measuring a target substance in a liquid sample comprising:
   a first hollow tubular member;
   a liquid-impermeable plastic disk arranged on said first member, said disk having an upper surface with a reaction area having an antibody or a fragment thereof which is reactive with said target substance on the upper surface of said disk;
   a second hollow tubular member, removably attachable to said first member, said second member having a liquid porous portion located above the reaction area of said first member when said second member is attached to said first member; and
   a boundary member which surrounds an edge of the reaction area in order to create a space between said upper surface of said disk and said lower surface of said second member, wherein said space the liquid sample volume is restricted to comprises a predetermined volume of not more than 5 µl.

2. The device according to claim 1, wherein a portion of said upper surface of said second member which extends beyond said edge of said reaction area is hydrophobic.

3. A device for measuring a target substance in a liquid sample comprising:
   a body having at least one reaction area on a substantially liquid impermeable sheet and an immobilized substance on said reaction area, which is reactive with the target substance in the liquid sample, and
   a porous member having at least one porous portion which is permeable to the liquid sample, said porous being disposed above said reaction area so as to contain a predetermined volume of not more than 5 µl of said liquid sample on said reaction area, wherein said immobilized substance is an antibody or a fragment thereof which is reactive with a tumor-associated antigen.

4. The device according to claim 3, wherein said porous member is circular and said porous portion is provided on the upper surface of said porous member.

5. The device according to claim 3, wherein said porous member is removably mounted on said body.

6. The device according to claim 3, wherein said liquid-impermeable sheet is made from a material selected from the group consisting of polyester, polypropylene and polyethylene.

7. The device according to claim 3, wherein said porous portion is made of nylon.

8. The device according to claim 3, wherein said tumor-associated antigen is a carcinoembryonic antigen.

9. The device according to claim 3, wherein said body further comprises a second reaction area for comparing a known substance in a second liquid sample.

10. A device for measuring a target substance in a liquid sample comprising:
    a body having
    at least one reaction area on a substantially liquid impermeable sheet;
    an immobilized substance on said reaction area, which is reactive with the target substance in the liquid sample;
    a base having a cylindrical form, said porous member being attached to the upper surface of said base; and
    a spacer which is attached to the upper surface of said liquid-impermeable sheet; and
    a porous member having at least one porous portion which is permeable to the liquid sample, said porous portion being disposed above said reaction area so as to contain a predetermined volume of not more than 5 µl of said liquid sample on said reaction area, wherein said immobilized substance is an antibody or a fragment thereof which is reactive with a tumor-associated antigen.

11. The device according to claim 10, wherein said porous member is removably mounted on said body.

12. The device according to claim 10, wherein said liquid-impermeable sheet is made from a material selected from the group consisting of polyester, polypropylene and polyethylene.

13. The device according to claim 10, wherein said porous portion is made of nylon.

14. The device according to claim 10, wherein said tumor-associated antigen is a carcinoembryonic antigen.

15. The device according to claim 10, wherein said body further comprises a second reaction area for comparing a known substance in a second liquid sample.

16. A method for measuring a target substance in a liquid sample by means of a device having:
    a body having at least one reaction area on a substantially liquid impermeable sheet and an immobilized substance on said reaction area, which is reactive to the target substance in the liquid sample; and
    a porous member having at least one porous portion which is permeable to the liquid sample, said porous being disposed above said reaction area so as to contain a predetermined volume of not more than 5 μl of said liquid sample on said reaction area wherein said immobilized substance comprises an antibody or fragment thereof which is reactive with a tumor-associated antigen;

comprising the steps of:

supplying said liquid sample through said porous portion onto said reaction area;

removing the excess volume of the liquid sample by contacting a remover with the excess volume of the liquid sample on said upper surface of said porous portion;

allowing said target substance to react with said immobilized substance;

rinsing unbound liquid from said reaction area;

removing said porous member form the device; and measuring said target substance on said reaction area.

17. The method according to claim 16, wherein said tumor-associated antigen is carcinoembryonic antigen.

18. The method according to claim 16, wherein said liquid sample is nipple discharge.

19. The method according to claim 18, wherein said breast nipple discharge is supplied to said porous portion of said device by placing said porous portion into direct contact with the outlet of a lactiferous duct of a patient.

20. A method for measuring a target substance in a liquid sample by means of a device comprising:

a body having at least one reaction area on a substantially liquid impermeable sheet;

an immobilized substance on said reaction area, which is reactive with the target substance in the liquid sample;

a base having a cylindrical form, said porous member being attached to the upper surface of said base;

a spacer which is attached to the upper surface of said liquid-impermeable sheet; and a porous member having at least one porous portion which is permeable to the liquid sample, said porous portion being disposed above said reaction area so as to contain a predetermined volume of not more than 5 μl of said liquid sample on said reaction area, wherein said immobilized substance comprises an antibody or a fragment thereof which is reactive with a tumor-associated antigen;

comprising the steps of:

supplying said liquid sample through said porous portion onto said reaction area;

removing the excess volume of the liquid sample by contacting a remover with the excess volume of the liquid sample on said upper surface of said porous portion;

allowing said target substance to react with said immobilized substance;

rinsing unbound liquid from said reaction area;

removing said porous member from the device; and measuring said target substance on said reaction area.

21. The method according to claim 20, wherein said tumor-associated antigen is carcinoembryonic antigen.

22. The method according to claim 20, wherein said liquid sample is nipple discharge.

23. The method according to claim 22, wherein said breast nipple discharge is supplied to said porous portion of said device by placing said porous portion into direct contact with the outlet of a lactiferous duct of a patient.

* * * * *